United States Patent
Taube et al.

(10) Patent No.: US 9,358,233 B2
(45) Date of Patent: *Jun. 7, 2016

(54) METHOD FOR TREATING ACUTE MYELOID LEUKEMIA

(75) Inventors: Tillmann Taube, Biberach an der Riss (DE); Gerd Munzert, Ulm (DE); Dorothea Rudolph, Vienna (AT)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 424 days.

This patent is subject to a terminal disclaimer.

(21) Appl. No.: 13/297,309

(22) Filed: Nov. 16, 2011

(65) Prior Publication Data

US 2012/0295864 A1 Nov. 22, 2012

(30) Foreign Application Priority Data

Nov. 29, 2010 (EP) .................................. 10192956

(51) Int. Cl.
*A61K 31/519* (2006.01)
*A61K 31/7068* (2006.01)
*A61K 31/4985* (2006.01)

(52) U.S. Cl.
CPC ............ *A61K 31/519* (2013.01); *A61K 31/7068* (2013.01); *A61K 31/4985* (2013.01)

(58) Field of Classification Search
CPC ............ A61K 31/519; A61K 31/7068; A61K 31/4985
See application file for complete search history.

(56) References Cited

U.S. PATENT DOCUMENTS

| | | | |
|---|---|---|---|
| 4,870,175 A | 9/1989 | Suzuki et al. |
| 4,957,922 A | 9/1990 | Lammens et al. |
| 5,043,270 A | 8/1991 | Abrams et al. |
| 5,167,949 A | 12/1992 | Ferrand et al. |
| 5,198,547 A | 3/1993 | Bailey et al. |
| 5,424,311 A | 6/1995 | Billhardt-Troughton et al. |
| 5,698,556 A | 12/1997 | Chan |
| 6,096,924 A | 8/2000 | Studer et al. |
| 6,156,766 A | 12/2000 | Arita et al. |
| 6,174,895 B1 | 1/2001 | Kleinman |
| 6,605,255 B2 | 8/2003 | Kroll et al. |
| 6,806,272 B2 | 10/2004 | Bauer et al. |
| 6,861,422 B2 | 3/2005 | Hoffmann et al. |
| 6,875,868 B2 | 4/2005 | Bonnert et al. |
| 6,960,589 B2 | 11/2005 | Cowart et al. |
| 7,238,807 B2 | 7/2007 | Duran et al. |
| 7,241,889 B2 | 7/2007 | Hoffmann et al. |
| 7,332,491 B2 | 2/2008 | Grauert et al. |
| 7,371,753 B2 | 5/2008 | Stadtmueller et al. |
| 7,414,053 B2 | 8/2008 | Grauert et al. |
| 7,439,358 B2 | 10/2008 | Linz et al. |
| 7,547,780 B2 | 6/2009 | Grauert et al. |
| 7,625,899 B2 | 12/2009 | Hoffmann et al. |
| 7,626,019 B2 | 12/2009 | Duran et al. |
| 7,629,460 B2 | 12/2009 | Grauert et al. |
| 7,638,627 B2 | 12/2009 | Kankan et al. |
| 7,700,769 B2 | 4/2010 | Grauert et al. |
| 7,723,517 B2 | 5/2010 | Grauert et al. |
| 7,728,134 B2 | 6/2010 | Linz et al. |
| 7,750,152 B2 | 7/2010 | Hoffman et al. |
| 7,759,347 B2 | 7/2010 | Hoffmann |
| 7,759,485 B2 | 7/2010 | Linz et al. |
| 7,807,831 B2 | 10/2010 | Grauert et al. |
| 7,816,530 B2 | 10/2010 | Grauert |
| 8,003,786 B2 | 8/2011 | Hoffmann et al. |
| 8,034,816 B2 | 10/2011 | Linz et al. |
| 8,058,270 B2 | 11/2011 | Munzert et al. |
| 8,138,341 B2 | 3/2012 | Linz et al. |
| 8,138,373 B2 | 3/2012 | Linz et al. |
| 8,143,247 B2 | 3/2012 | Munzert et al. |
| 8,188,086 B2 | 5/2012 | Linz et al. |
| 8,193,188 B2 | 6/2012 | Hoffmann et al. |
| 8,202,867 B2 | 6/2012 | Linz et al. |
| 8,329,695 B2 | 12/2012 | Linz et al. |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2003/0162790 A1 | 8/2003 | Cowart et al. |
| 2004/0024205 A1 | 2/2004 | Borredon et al. |
| 2004/0029885 A1 | 2/2004 | Bauer et al. |
| 2004/0127504 A1 | 7/2004 | Cowart et al. |
| 2004/0147524 A1 | 7/2004 | Bauer et al. |
| 2004/0176380 A1 | 9/2004 | Hoffmann et al. |

(Continued)

FOREIGN PATENT DOCUMENTS

CA 2458699 A1 3/2003
CA 2517020 A1 9/2004

(Continued)

OTHER PUBLICATIONS

Phys. Org. New ways of Inhibiting cell cycle shows promise, 2008, pp. 1-2.*
Bug et al. Blood, Nov. 19, 2010,vol. 116, pp. 1-2.*
Organic Chemistry, Grupo Editorial Iberoamerica, Section 13, 3, pp. 301-302, 1983.
Roberts, Jr., T. G. et al. "Trends in the Risks and Benefits to Patients with Cancer Participating in Phase 1 Clinical Trials". JAMA, Nov. 3, 2004, vol. 292, No. 17, p. 2130-2140.
Rocha Lima, C.M. et al. "Randomized phase II trial of gemcitabine plus irinotecan or docetaxel uin stage IIIB or stage IV NSCLC" Annals of Oncology, 15(3), p. 410-418, 2004.
Rylander, P.N. "Hydrgenation Methods". 1985, Chapter 13.
Rylander, P.N. "Hydrgenation Methods". 1985, Chapters 3, 4.

(Continued)

*Primary Examiner* — Samira Jean-Louis
(74) *Attorney, Agent, or Firm* — Michael P. Morris; Atabak R. Royaee; Usha R. Patel

(57) ABSTRACT

The present invention relates to the use of BI 6727 or a salt thereof or the hydrate thereof for treating patients suffering from acute myeloid leukemia (AML) comprising the administration of a high dose of BI 6727 according to a specific dosage schedule, optionally in combination with cytarabine.

9 Claims, No Drawings

(56) References Cited

U.S. PATENT DOCUMENTS

| | | |
|---|---|---|
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0063735 A1 | 3/2006 | Redkar et al. |
| 2006/0074088 A1 | 4/2006 | Munzert et al. |
| 2006/0079503 A1 | 4/2006 | Schwede et al. |
| 2007/0043055 A1 | 2/2007 | Maier et al. |
| 2007/0117776 A1 | 5/2007 | Lyons |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0029990 A1 | 1/2009 | Maier et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2009/0306101 A1 | 12/2009 | Solca et al. |
| 2010/0029642 A1 | 2/2010 | Hoffmann et al. |
| 2010/0179134 A1 | 7/2010 | Singh et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |
| 2011/0046176 A1 | 2/2011 | Moore, II et al. |
| 2012/0107312 A1 | 5/2012 | Munzert et al. |
| 2012/0214995 A1 | 8/2012 | Linz et al. |
| 2012/0238754 A1 | 9/2012 | Schnaubelt et al. |
| 2012/0295864 A1 | 11/2012 | Taube et al. |
| 2012/0296091 A1 | 11/2012 | Sieger et al. |
| 2012/0329803 A1 | 12/2012 | Linz et al. |
| 2013/0012465 A1 | 1/2013 | Haslinger et al. |

FOREIGN PATENT DOCUMENTS

| | | |
|---|---|---|
| CA | 2517010 A1 | 11/2004 |
| CA | 2576290 A1 | 2/2006 |
| EP | 143478 A1 | 6/1985 |
| EP | 347146 A2 | 12/1989 |
| EP | 399856 A1 | 11/1990 |
| EP | 429149 A1 | 5/1991 |
| ES | 2287583 | 12/2007 |
| JP | 2009169737 A | 6/1997 |
| RU | 2002125451 A | 1/2004 |
| WO | 9608537 A1 | 3/1996 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 0119825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A1 | 10/2002 |
| WO | 03020722 A1 | 3/2003 |
| WO | 03093249 A1 | 11/2003 |
| WO | 2004014899 A1 | 2/2004 |
| WO | 2004024728 A2 | 3/2004 |
| WO | 2004076454 A1 | 9/2004 |
| WO | 2004093848 A2 | 11/2004 |
| WO | 2005067935 A1 | 7/2005 |
| WO | 2006005510 A1 | 1/2006 |
| WO | 2006018182 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2006021379 A1 | 3/2006 |
| WO | 2006021547 A1 | 3/2006 |
| WO | 2007014838 A1 | 2/2007 |
| WO | 2007054551 A1 | 5/2007 |
| WO | 2007090844 A1 | 8/2007 |
| WO | 2009019205 A1 | 2/2009 |
| WO | 2009112524 A1 | 9/2009 |
| WO | 2010111172 A1 | 9/2010 |
| WO | 2011101369 A1 | 8/2011 |
| WO | 2012049153 A1 | 4/2012 |
| WO | 2012072505 A1 | 6/2012 |
| WO | 2012156283 A1 | 11/2012 |
| WO | 2012156380 A1 | 11/2012 |

OTHER PUBLICATIONS

Rylander, P.N. "Hydrgenation Methods". 1985, Chapters 8, 9, 10, 11.

Rylander, P.N. "Hydrgenation Methods". 1985, Chapter 5, 6, 7.

Rylander, P.N., "Hydrogenation Methods". 1985, Chapters 1, 2.

Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.

Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.

Science, vol. 310, Oct. 21, 2005, p. 409, Chemistry: One After Another.

Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.

Souillac, P. et al., "Characterization of delivery systems, differential scanning calorimetry". (In Encyclopedia of Controlled Drug Delivery), 1999, John Wiley & Sons, pp. 212-227.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21—pp. 129-133.

Takai, N. et al., "Polo-like kinases (PLKs) and cancer". Oncogene, 2005, 24, pp. 287-291.

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

Turner, S., "The Design of Organic Syntheses". Elsevier, 1976, pp. 10 and 149.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

(56) References Cited

OTHER PUBLICATIONS

Visiting Nurse Association of America. www.vnaa.org/gen/Germ_Protection_Center_Cold_and_Flu_Resources,html, 2009.
Voskoglou-Nomikos, T. et al., "Clinical predictive value of the in vitro cell line, human xenograft, and mouse allograft preclinical cancer models". Clinical Cancer Research vol. 9, 2003, pp. 4227-4239.
Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.
Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.
Webster's Comprehensive Dictionary, 1996, pp. 1013-1014.
Wikipedia. "Melting Point", Jan. 17, 2007. http://en.wikipedia.org/wiki/Melting_point.
Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.
ACPS Meeting, Background Information. "Scientific considerations of plymorphisnn in pharmaceutical solids: abbreviated new drug applications". Oct. 2002.
Ahlenius, T. List of cardiovascular disorder/diseases. Ahlenius, Karolinska Institutet. Stockholm, Sweden. Cardiovascular Diseases, p. 1-34, Apr. 2007.
Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.
Arnold, K. "Collaboration to play key role in NCI's future, director says". Journal of the National Cancer Institute, Jun. 5, 2002, pp. 790-792, vol. 94, No. 11.
BBC News/Health, Killer Breast Cancern Therapy Hope, www.newsvote.bbc/co./uk, Published Jan. 21, 2006.
Bennett, J.C., et al., "Textbook of Medicine", Part XIV, Oncology, 1997.
Beshore, D.C.et al., "Preparation of Substituted Piperazinones via Tandem Reductive Amination-N.N-Acyl Transfer)—Cyclization". Organic Letters, 2002, vol. 4, No. 7, p. 1201-1204.
Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.
Cancer Drug Design and Discovery, Stephen Neidle, Ed. (Elsevier/Academic Press, 2006), p. 427-431.
Chen, J.X. et al., "Parallel differentiated recognition of ketones and acetals". Angewandte Chemie Int. Ed, vol. 37, Issue 1/2, p. 91-93, 1998.
Dipolar aprotic solvent. Exhibit A, IUPAC Compendium of Chemical Terminology, 2nd Edition, 1997.
Doerwald, F.Z. Book Wiley-VCH Verlag GmbH & Co. KGaA, "Side reactions in organice synthesis: A Guide to Successful Synthesis Design". 2005.
Dyson, G, et al. "The Chemistry of Synthetic Drugs". 1964, p. 12-19.
Eurasian Opinion, Appln No. 2007/00389/28, Maly Slatoustinsky per., d.10, kv.15, 101000 Moscow, Russia, "EVROMARKPAT", 2007.
Expert Scientific Group on Phase One Clinical Trials, Final Report, Nov. 30, 2006, p. C1, C35-C38.
Ferrand, G., et al., "Synthesis and potential antiallergic activity of new pteridinones and related compounds". Eur. J. Med. Chem, 31, 1996, pp. 273-280. XP—2246920.
Ghandi, L., et al., "An Open-Label Phase II Trial of the PLK Inhibitor BI 2536 in Patients with Sensitive Relapse Small Cell Lung Cancer". ASCO Meeting 2009.
Giron, G. "Thernal analysis and calorimetric methods in the characterization of plymorphs and solvates". Thermochimica Acta 248, 1995, pp. 1-59.
Goodman-Gilman's "The Pharmacological Basis of Therapeutics". Ninth edition, 1996, pp. 1225-1271.
Gura, T. "Cancer Models: Systems for Identifying New Drugs are Often Faulty". Science, Nov. 7, 1997, vol. 278, No. 5340—p. 1041-1042.
Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.
Jamieson, C. et al., "Application of ReactArray Robotics and Design of Experiments Techniques in Optimisation of Supported Reagent Chemistry". Org. Proc. Res. & Dev., 2002, 6, p. 823-825.
Jaworska, J., et al., "Review of methods for assessing the applicability domains of SARS and QSARS". Sponsor: The European Commission—Joint Research Ctr., Institute for Health and Consumer Protection—ECVAM, Italy, 2004.
Kamb, A. "What's wrong with our cancer models?". Nature Reviews Drug Discovery, vol. 4, Feb. 2005, p. 161-165.
Kashima, M. K. et al., "Expression of polo-like kinase (PLK1) in non-Hodgkin's lymphomas". NCBI, PubMed, 2005.
Kimball, S. D. et al., "Cell cycle kinases and checkpoint regulation in cancer". Annual Reports in Medicinal Chemistry, 36, Chapter 14, 2001, pp. 139-148.
Kola, I. et al., "Can the phamaceutical industry reduce attrition rates?" Nature Reviews Drug Discovery, vol. 3, Aug. 2004, p. 711-715.
Krause, M. et al., "Combination of Radiation and Polo-like Kinase 1 Inhibition with BI 6727 in tumour model A431". Strahlenther Onkol, 187, S1, 53 (v17-6), 2011.
Kummer B, et al., "Combination of Radiation and Polo-like Kinase 1 Inhibition with BI6727 in tumour model A431". Vortrag. 20. Symposium „Experimentelle Strahlentherapie und klinische Strahlenbiologie, Exp. Strahlenther. Klin. Strahlenbiol. 20: 93-96 (2011) (Lecture 20, Symposium Experimental Radiation Therapy and Clinical Radiation Biology.)
Kummer, B. et al., Presentation: "Combination of irradiation and polo-like kinase 1 inhibition with BI 6727 in tumour model A 431". OncoRay—National Centre for Radiation Research in Oncology, Dresden 2011, Experimental Radiotherapy and Clinical Radiobiology.
Leaf, C. et al., "Why are we losing the war on cancer (and how to win it)". Health Administrator, vol. XVII, No. 1, 2005, p. 172-183.
Leukemia & Lymphoma Society—Disease Information-Lymphoma. www.leukemia-lymphoma.org/all_page?item_id-7030, 2008.
Leukemia & Lymphoma Society—Disease Information. www.leukemia-lymphoma.org/all_page?item_id-7026, 2008.
Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.
Mashkovkii, M.D., "Medicaments". Moscow, Novaja Volna, 2001, vol. 1, p. 11.
Mashkovskii, M.D. "Drugs", Handbook for Doctors, 1993, Part I, Ch.1, p. 8.
Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.
Mayer, SF, et al., "Enzyme-initiated domino (cascase) reactions". Chem. Soc. Rev, 2001, p. 332-339.
MedlinePlus: Bacterial Infections. www.nim.nih.gov/medlineplus/print/bacterialinfections.htm, date last updated Mar. 25, 2009.
MedlinePlus: Viral Infections. www.nim.nih.gov/medlineplus/print/viralinfections.htm, date last updated Feb. 11, 2009.
Merck Manual of Medical Information—Home Edition, Section 17. "Parasitic Infections". Chapter 184, 2003.
Mikhailov, I.B., Principles of Rational Pharmacotherapy. Handbook for clinical pharmacology for students of pediatric and medical faculties of medical high schools, St. Petersburg, Russia, "Foliant", 1999, p. 25.
Mito, K., et al., "Expression of polo-like kinase (PLK1) in non-Hodgkin's lymphomas". NCBI, PubMed, 2005, Leuk. Lymphoma, 46(2), pp. 251-231.

(56) References Cited

OTHER PUBLICATIONS

Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
Neidle, S. ed., "Cancer Drug Design and Discovery", Elsevier/Academic Press, 2008, p. 427-431.
Norman, P. "PDE4 inhibitors". Ashley Publications Ltd., Expert Opinions Ther. Patents, 1999, pp. 1101-1118.
Office Action mailed Dec. 10, 2003 for U.S. Appl. No. 10/226,710, filed Aug. 23, 2002. Inventor: Eckhart Bauer.
Office Action mailed Apr. 28, 2004 for U.S. Appl. No. 10/374,876, filed Feb. 26, 2003. Inventor: Matthias Hoffmann.
Ohio Dept of Health, "Brain and Other Central Nervous System Cancer in Ohio, 1997-2001". Sep. 2004, pp. 1-4.
Clinical Trials: NCT01348347. BI6727 (Volasertib) Monotherapy Phase I Trial in Japanese Patients with Advanced Soliid Tumours. Apr. 29, 2011 [Retrieved from the Internet: URL: http://www.clinicaltrials.gov./ct2/show/NCT01348347?term=volasertib&rank=1] retrieved Jul. 16, 2012.
Ellis, P.M. et al., "A Phase I Open-Label Dose-Escalation Study of Intravenous BI 2536 Together with Pemetrexed in Previously Treated Patients with Non-Small-Cell Lung Cancer" Clinical Lung Cancer, 2012, p. 1-9.
International Search Report and Written Opinion for PCT/EP2011/071008 mailed Feb. 28, 2012.
Medema et al.; Polo-like Kinase 1 Inhibitors and Their Potential Role in Anticancer Therapy, with a Focus on NSCL; Clinical Cancer Research; 2011; vol. 17; No. 20; pp. 6459-6466.
Mross, K. et al., A randomised phase II trial of the polo-like kinase inhibitor BI 2536 in chemo-naieve patients with unresectable exocrine adenocarcinoma of the pancreas—a study within the Central European Society Anticancer Drug research (CESAR) collaaborative work. British Journal of Cancer, 2012, p. 1-7.
Rudolph et al., BI 6727, a Polo-like kinase inhibitor with improved pharmacokinetic profile and broad antitumor activity, Clinical Cancer Research, 2009.
Rudolph, D. et al., "430 Poster Characterization of BI 6727, a novel Polo-like kinase inhibitor with a distinct pharmacokinetic profile and efficacy in a model of taxane-resistant colon cancer". European Journal of Cancer. Supplement, Pergamon, Oxford, GB, vol. 6, No. 12, Oct. 1, 2008, p. 135. [retrieved on Oct. 1, 2008].
Schoffski et al., Polo-Like Kinase (PLK) Inhibitors in Preclinical and Early Clinical Development in Oncology, The Oncologist, 2009, 14:559-570.
Schoffski, P., "Polo-like kinase (PLK) inhibitors in preclinical and early clinical development in oncology", The Oncologist, vol. 14, 2009, pp. 559-570.
Schoffski, P., et al., "A phase I single dose escalation study of the novel polo-like kinase 1 inhibitor BI 6727 in patients with advanced solid tumours", EJC Supplement, vol. 6. No. 12, Oct. 2008, p. 14-15.
Xu, W-J., "Efficient Inhibition of Human Colorectal Carcinoma Growth by RNA Interference Targeting Polo-Like Kinase 1 In Vitro and In Vivo." Cancer Biotherapy and Radiopharmaceuticals, 2011, vol. 26, No. 4, pp. 427-436.
"Salt Forms of Drug Absorption", Swarbrick, et al. editors, Encyclopedia of Pharm. Tech. 13 Marcel Dekker, NY, 1996, 453-499.
Badavvy, S. I. et al., "Sale Selection for Phamaceutical Compounds", Preformulation in Solid Dosage Form Develolpment, Infoa Healthcare 2008, Chapter 2.3, 63-80.
Bastin, R. J. et al., "Salt Selection and Optimisation Procedures for Pharmaceutical New Chemical Entities", Organic Process Research and Development, 2000, 4,427-435.
Goodman and Gilman 9th Edition; 1996; pp. 1225-1232 and 1269-1271.
Gould, P. L., "Salt selection for basic drugs", International Journal of Pharmaceutics, 33(1986), 201-217.

Lin, C-C et al., "A phase I study of two dosing schedules of volasertib (BI 6727), an intravenous polo-like kinase inhibitor, in patients with advanced solid malignancies." British Journal of Cancer, 2014, pp. 1-7.
Morris, K.R. et al., "An integrated approach to the selection of optimal salt form for a new drug candidate", International Journal of Pharmaceutics, 105, 1994, 209-217.
Neau, S. H., Pharmaceutical Salts, CRC Press, 2008, Ch 17, p. 417-435.
Rudolph, D. et al., "BI 6727, a Polo-like Kinase Inhibitor with Improved Pharmacokinetic Profile and Broad Antitumor Activity." Clinical Cancer Research, 2009, vol. 15, No. 9, pp. 3094-3102 (Updated Full Text).
Schoffski, P. et al., "A phase I, dose-escalation study of the novel Polo-like kinase inhibitor volasertib (BI 6727) in patients with advanced solid tumors." European Journal of Cancer, 2012, vol. 48, pp. 179-186.
Serajuddin, Abu T.M., "Salt formation to improve durg solubility", Advanced Drug Delivery Reviews, 59, 2007, 603-616.
Awada, A. et al., "Phase I trial of volasertib, a Polo-like kinase inhibitor, plus platinum agents in solid tumors: safety, pharmacokinetics and activity." Invest New Drugs, 2015, vol. 33, No. 3, pp. 611-620.
Benetatos, L. et al., "Polo-like kinase 2 (SNK/PLK2) is a novel epigenetically regulated gene in acute myeloid leukemia and myelodysplastic syndromes: genetic and epigenetic interactions." Annals of Hematology, 2011, vol. 90, No. 9, pp. 1037-1045.
Berg, T. et al., "Polo-like kinases in AML." Expert Opinion on Investigational Drugs, 2012, vol. 21, No. 8, pp. 1069-1074.
Boulikas, T. et al., "Recent clinical trials using cisplatin, carboplatin and their combination chemotherapy drugs (Review)." Oncology Reports, 2004, vol. 11, pp. 559-595.
Christoph, D. et al., "Polo-like kinase 1 inhibitors in mono-and combination therapies: a new strategy for treating malignancies." Expert Review of Anticancer Therapy, 2011, vol. 11, No. 7, pp. 1115-1130.
Gil, T. et al., "Final analysis of a phase I single dose-escalation study of the novel polo-like kinase 1 inhibitor BI 6727 in patients with advanced solid tumors." 2010 ASCO Annual Meeting, Journal of Clinical Oncology, Poster Abstract No. 3061.
Goodman & Gilman's The Pharmacological Basis of Therapeutics, Tenth Edition, Chapter 1 "Pharmacokinetics: The Dynamics of Drug Absorption, Distribution, and Elimination." 2001, pp. 3-29.
Seetharam, M. et al., "Treatment of higher risk myelodysplastic syndrome patients unresponsive to hypomethylating agents with ON 01910.Na." Leukemia Research, 2012, vol. 36, pp. 98-103.
Abstract in English for JP09169737, Date of Publication: Jun. 30, 1997, Applicant Tosoh Corp, Inventor: K. Hiroyuki, Title: Production of N-Methylimidazoles. Date filed: Dec. 21, 1995.
International Seach Report for PCT/EP2007/051139 mailed May 29, 2007.
International Search Report and Written Opinion for PCT/EP2005/008623 mailed Nov. 23, 2005.
International Search Report and Written Opinion for PCT/EP2005/008626 mailed Feb. 10, 2006.
International Search Report and Written Opinion for PCT/EP2008/060112 mailed Nov. 6, 2008.
International Search Report and Written Opinion for PCT/EP2011/052280 mailed Apr. 29, 2011.
International Search Report and Written Opinion for PCT/EP2011/067696 mailed Nov. 4, 2011.
International Search Report and Written Opinion for PCT/EP2012/058704 mailed Aug. 8, 2012.
International Search Report and Written Opinion for PCT/EP2014/065937 mailed Oct. 6, 2014.
International Search Report and Written Opinion for PCT/EP2014/065938 mailed on Sep. 9, 2014.
International Search Report and Written Opinion for PCT/EP2014/065939 mailed Sep. 9, 2014.
International Search Report and Written Opinion for PCT/EP2015/072386 mailed Dec. 2, 2015.
International Search Report for PCT/EP03/01935 mailed Jul. 23, 2003.

(56) References Cited

OTHER PUBLICATIONS

International Search Report for EP2005/007347 mailed Oct. 18, 2005.
International Search Report for PCT/EP2005/006404 mailed Nov. 14, 2005.
International Search Report for PCT/EP2005/007532 mailed Oct. 6, 2005.
International Search Report for PCT/EP2005/008734. mailed Aug. 25, 2006.
International Search Report for PCT/EP2005/008735 mailed Dec. 8, 2005.
International Search Report for PCT/EP2005/008736 mailed Nov. 30, 2005.
International Search Report for PCT/EP2005/008990 mailed Dec. 13, 2005.
International Search Report for PCT/EP2005/008991 mailed Dec. 15, 2005.
International Search Report for PCT/EP2005/054096 mailed Jan. 24, 2006.
International Search Report for PCT/EP2005/054099 mailed Dec. 15, 2005.
International Search Report for PCT/EP2005/056291 mailed Mar. 21, 2006.
International Search Report for PCT/EP2006/064305 mailed Oct. 16, 2006.
X-ray Diffraction—Factors that affect d's and I's. [Downloaded from the internet Mar. 9, 2011, URL: http://www.gly.uga.edu/Schroeder/geol6550/XRD.html].

* cited by examiner

METHOD FOR TREATING ACUTE MYELOID LEUKEMIA

The present invention relates to the use of BI 6727 or a salt thereof or the hydrate thereof for treating patients suffering from acute myeloid leukemia (AML) comprising a high dose of BI 6727 administered according to a specific dosage schedule, optionally in combination with cytarabine.

BACKGROUND OF THE INVENTION

Acute myeloid leukemia (AML), also known as acute myelogenous leukemia, is a cancer of the myeloid line of blood cells, characterized by the rapid growth of abnormal white blood cells that accumulate in the bone marrow and interfere with the production of normal blood cells. As an acute leukemia, AML progresses rapidly and is typically fatal within weeks or months if left untreated. AML is the most prevalent form of adult leukemia, particularly among the elderly and is slightly more common in men than women. There is an estimated prevalence of 30,000 cases of AML in the US and 47,000 in the EU.

The incidence of AML increases with age with a median age at diagnosis of 67 years. The global incidence CAGR for AML out to 2013 is 1.4%. An aging population, along with an increased incidence of treatment-related AML in cancer survivors, currently accounting for 10-20% of all AML cases, is expected to drive the incidence of AML. In addition, there is some geographic variation in the incidence of AML. In adults, the highest rates are seen in North America, Europe, and Oceania, while adult AML is rarer in Asia and Latin America.

AML accounts for approximately 1.2% of all cancer deaths. The 5 year survival rates for AML are low, driven by therapy failure and patients relapsing. Among patients <65 the 5 year survival rate is 34.4%, among patients >65 it is only 5%.

According to the French-American-British (FAB) classification system AML is divided into subtypes (M0 to M8), based on the type of cell from which the leukemia developed and its degree of maturity. The WHO classification incorporates of genetic abnormalities into diagnostic algorithms for the diagnosis of AML. This classification is done by examining the appearance of the malignant cells under light microscopy and by using cytogenetics and molecular genetics to characterize any underlying chromosomal abnormalities or genetic changes. The subtypes impact on prognoses, responses to therapy and treatment decisions.

The WHO subtypes are as follows:
Acute Myeloid Leukemia and Related Neoplasms
  Acute myeloid leukemia with recurrent genetic abnormalities
    AML with t(8;21)(q22;q22); RUNX1-RUNX1T1
    AML with inv(16)(p13.1q22) or t(16;16)(p13.1;q22); CBFB-MYH11
    APL with t(15;17)(q22;q12); PML-RARA
    AML with t(9;11)(p22;q23); MLLT3-MLL
    AML with t(6;9)(p23;q34); DEK-NUP214
    AML with inv(3)(q21 q26.2) or t(3;3)(q21;q26.2); RPN1-EVI1
    AML (megakaryoblastic) with t(1;22)(p13;q13); RBM15-MKL1
    Provisional entity: AML with mutated NPM1
    Provisional entity: AML with mutated CEBPA
  Acute myeloid leukemia with myelodysplasia-related changes
  Therapy-related myeloid neoplasms
  Acute myeloid leukemia, not otherwise specified
    AML with minimal differentiation
    AML without maturation
    AML with maturation
    Acute myelomonocytic leukemia
    Acute monoblastic/monocytic leukemia
    Acute erythroid leukemia
      Pure erythroid leukemia
      Erythroleukemia, erythroid/myeloid
    Acute megakaryoblastic leukemia
    Acute basophilic leukemia
    Acute panmyelosis with myelofibrosis
  Myeloid sarcoma
  Myeloid proliferations related to Down syndrome
    Transient abnormal myelopoiesis
    Myeloid leukemia associated with Down syndrome
  Blastic plasmacytoid dendritic cell neoplasm The efficacy of chemotherapeutic agents can be improved by improving the dosage schedule and/or using combination therapies with other compounds. Even if the concept of combining several therapeutic agents or improved dosage schedules already has been suggested, there is still a need for new and efficient therapeutic concepts for the treatment of cancer diseases, which show advantages over standard therapies.

BI 6727 is a highly potent and selective inhibitor of the serine-threonine Polo like kinase 1 (Plk1), a key regulator of cell-cycle progression. BI 6727 is a second-generation dihydropteridinone derivative with distinct pharmacokinetic (PK) properties. The problem underlying this invention was to develop improved dosage schedules for monotherapy and combinations of BI 6727 and cytarabine in AML with maximal activity and limited toxicity.

BI 6727 (I) is known as the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide,

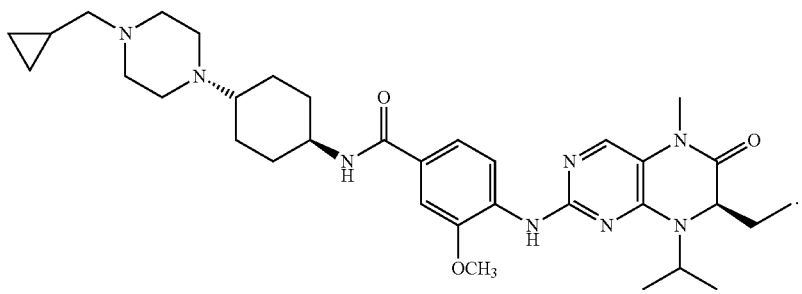

(I)

This compound is disclosed in WO 04/076454. Furthermore, trihydrochloride salt forms and hydrates thereof are known from WO 07/090,844. They possess properties which make those forms especially suitable for pharmaceutical use. The above mentioned patent applications further disclose the use of this compound or its monoethanesulfonate salt for the preparation of pharmaceutical compositions intended especially for the treatment of diseases characterized by excessive or abnormal cell proliferation.

Cytarabine is inter alia known by the brand names Cytosar-U, Tarabine PFS, DepoCyte and AraC. Cytarabine is mainly used in the treatment of acute myeloid leukaemia, acute lymphocytic leukaemia (ALL) and in lymphomas.

SUMMARY OF THE INVENTION

In clinical trials with patients suffering from AML it has been found that BI 6727 can be administered in higher dosages and shorter intervals than in patients with solid tumors. In addition it has been found that BI 6727 can be administered in these higher dosages and shorter intervals in combination with Cytarabine, which has a profile of side effects which is similar to that of BI 6727 without potentiation of those side effects.

Accordingly, a first object of the present invention is a method of treating AML in patients suffering from AML characterized by administering 350 to 500 mg, preferably 350, 400, 450 or 500 mg of BI 6727 or a pharmaceutically acceptable salt thereof or a hydrate thereof per administration. Preferably equal doses of BI 6727 are administered at least two days during a 4 week treatment cycle, preferably at day 1 and at one of the days 7, 8, 9, 10, 11, 12, 13, 14, 15, 16, 17, 18, 19, 20 or 21, more preferably at day 1 and at day 15, during a 4 week treatment cycle.

Another object of the present invention refers to BI 6727 or a pharmaceutically acceptable salt thereof or a hydrate thereof for the use in treating AML in patients suffering from AML characterized by administering 350 to 500 mg, preferably 350, 400, 450 or 500 mg of BI 6727 per administration. Preferably equal doses of BI 6727 are administered at least two days during a 4 week treatment cycle, preferably at day 1 and at one of the days 7, 8, 9, 10, 11, 12, 13, 14, 15, 16, 17, 18, 19, 20 or 21, more preferably at day 1 and at day 15, during a 4 week treatment cycle.

Another object of the present invention refers to the use of BI 6727 or a pharmaceutically acceptable salt thereof or a hydrate thereof for the manufacture of a medicament for treating AML wherein the medicament is prepared for administration of 350 to 500 mg, preferably 350, 400, 450 or 500 mg of BI 6727 per administration. Preferably equal doses of BI 6727 are administered at least two days during a 4 week treatment cycle, preferably at day 1 and at one of the days 7, 8, 9, 10, 11, 12, 13, 14, 15, 16, 17, 18, 19, 20 or 21, more preferably at day 1 and at day 15, during a 4 week treatment cycle.

Another object of the present invention is a method of treating AML characterized by a dosage schedule (I) comprising or consisting of
 a) administration of an effective amount of BI 6727 or a pharmaceutically acceptable salt thereof or a hydrate thereof at least two days during a 4 week treatment cycle and
 b) administration of an effective amount of Cytarabine at least at one day of the said 4 week treatment cycle
to a patient suffering from AML.

Another object of the present invention is a method of treating AML in patients suffering from AML (dosage schedule (II)) characterized by dosage schedule (I) wherein BI 6727 or a pharmaceutically acceptable salt thereof or a hydrate thereof is administered at day 1 and at one of the days 7, 8, 9, 10, 11, 12, 13, 14, 15, 16, 17, 18, 19, 20 or 21 during a 4 week treatment cycle.

A another object of the present invention is a method of treating AML in patients suffering from AML (dosage schedule (III)) characterized by one of the above dosage schedules (dosage schedule (I) or (II)) wherein 350 to 500 mg, preferably 350, 400, 450 or 500 mg, most preferably 350 mg of BI 6727 or a pharmaceutically acceptable salt thereof or a hydrate thereof are administered per day of administration.

Another object of the present invention is a method of treating AML in patients suffering from AML (dosage schedule (IV)) characterized by one of the above dosage schedules (dosage schedule (I), (II) or (III)) wherein Cytarabine is administered at 10 days of the said 4 week treatment cycle.

Another object of the present invention is a method of treating AML in patients suffering from AML (dosage schedule (V)) characterized by one of the above dosage schedules (dosage schedule (I), (II), (III) or (IV)) wherein Cytarabine is administered from day 1 to 10 of the said 4 week treatment cycle.

Another object of the present invention is a method of treating AML in patients suffering from AML (dosage schedule (VI)) characterized by one of the above dosage schedules (dosage schedule (I), (II), (III), (IV) or (V)) wherein 40 mg Cytarabine are administered per day of administration.

Another object of the invention refers to BI 6727 or a pharmaceutically acceptable salt thereof or a hydrate thereof for the use in treating AML in patients suffering from AML characterized in that BI 6727 or a pharmaceutically acceptable salt thereof or a hydrate thereof is administered according to one of the dosage schedules (I) to (VI).

Another object of the invention refers to Cytarabine for the use in treating AML in patients suffering from AML characterized in that Cytarabine is administered according to one of the dosage schedules (I) to (VI).

Another object of the invention refers to the use of BI 6727 or a pharmaceutically acceptable salt thereof or a hydrate thereof for the manufacture of a medicament for treating AML in patients suffering from AML wherein the medicament is prepared for administration according to one of the dosage schedules (I) to (VI).

Another object of the invention refers to the use of Cytarabine for the manufacture of a medicament for treating AML in patients suffering from AML wherein the medicament is prepared for administration according to one of the dosage schedules (I) to (VI).

Another object of the invention is a pharmaceutical composition comprising an effective amount of BI 6727 and an effective amount of Cytarabine together with an instruction for administration of both active ingredients to a patient suffering from AML, wherein according to said instruction BI 6727 is to be administered according to the above mentioned dosage schedules.

Another object of the invention is a pharmaceutical kit, comprising a first compartment which comprises an effective amount of BI 6727 and a second compartment which comprises an effective amount of Cytarabine, together with an instruction for administration of both active ingredients to a patient suffering from AML, wherein according to said instruction BI 6727 (preferably 350, 400, 450 or 500 mg, more preferably 350 mg) and Cytarabine (preferably 40 mg/day) is to be administered according to one of the above mentioned dosage schedules.

Another object of the present invention is the compound BI 6727 for its coadministration with Cytarabine to a patient suffering from AML, characterized in that BI 6727 (preferably 350, 400, 450 or 500 mg, more preferably 350 mg) and Cytarabine (preferably 40 mg/day) is to be administered according to above mentioned dosage schedules.

Another object of the present invention is the use of BI 6727 for preparation of a pharmaceutical composition comprising an effective amount of BI 6727 and Cytarabine together with an instruction for administration of both active ingredients to a patient suffering from AML, wherein according to said instruction BI 6727 (preferably 350, 400, 450 or 500 mg, more preferably 350 mg) and Cytarabine (preferably 40 mg/day) is to be administered according to above mentioned dosage schedules.

Another object of the present invention is the use of BI 6727 for preparation of a pharmaceutical kit, comprising a first compartment which comprises an effective amount of BI 6727 and a second compartment which comprises Cytarabine, optionally together with an instruction for administration of both active ingredients to a patient suffering from AML, wherein according to said instruction BI 6727 (preferably 350, 400, 450 or 500 mg, more preferably 350 mg) and Cytarabine (preferably 40 mg/day) is to be administered according to above mentioned dosage schedules.

DETAILED DESCRIPTION OF THE INVENTION

For example, the administration of BI 6727 at least two days during a 4 week treatment cycle means that BI 6727 is administered at two different days during a 4 week treatment.

The administration of an effective amount of Cytarabine at least one day of the said 4 week treatment cycle means that during the 4 week treatment cycle in which BI 6727 is administered at least two times, also Cytarabine is administered at least at one day.

The administration of BI 6727 at day 1 and 15 during a 4 week treatment cycle means that one dosage of BI 6727 or a pharmaceutically acceptable salt or a hydrate thereof is administered at day one and the second dosage is administered at day 15 to the patient suffering from AML in the four week treatment cycle.

The administration of Cytarabine from days 1 to 10 during a 4 week treatment cycle means that a daily dosage of Cytarabine or a pharmaceutically acceptable salt thereof is administered to the patient suffering from AML beginning at day one and ending with the last dosage at day 10 in the four week treatment cycle.

Accordingly a complete four week treatment cycle according to one of the above mentioned dosage schedules may comprise the following administrations:

Day 1: one dosage of BI 6727 (e.g. 350 mg) and two dosages of Cytarabine (20 mg bid);
Day 2 to day 10 (including): two dosages of 20 mg Cytarabine per day;
Day 11 to day 14 (including): no administration of BI 6727 and Cytarabine;
Day 15: one dosage of BI 6727 (e.g. 350 mg);
Day 16 to day 28 (including): no administration of BI 6727 and Cytarabine.

This treatment cycle can be repeated as long as patients are eligible for repeated cycles, i.e. until progression of disease and as long as neither patient nor investigator requests treatment discontinuation.

The instruction for coadministration may be in any form suitable for pharmaceuticals, e.g. in form of a leaflet added to the dosage form within secondary packaging or an imprint on the primary or secondary packaging.

Dosages/BI 6727:

For intravenous treatment BI 6727 may be administered to the human patient in a daily dose of 350 to 500 mg/application, preferably 350, 400, 450 or 500 mg/application, particularly preferred in combination with cytarabine (20 mg bid days 1-10) at a dose of 350 mg/application. For instance, BI 6727 can be administered as a slow intravenous infusion over several hours, e.g. over about 1, 2, 4, 6, 10, 12 or 24 hours, preferably about 1 or 2 hours.

Dosages/Cytarabine:

Cytarabine may be administered daily in a total dose of 10 to 150 mg, e.g 20, 30, 40, 50 mg one or two times daily or 10, 20, 30, 40, 50, 60, 70, 80, 90, 100, 110, 120, 130, 140 or 150 mg once a day. The total daily dose may also be divided into two or three subdoses to be taken within one day. Preferably, the oral daily dose is administered in a single dose of 40 mg or in two doses of 20 mg each.

However, it may optionally be necessary to deviate from the dosage amounts specified for BI 6727 and Cytarabine, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses. For example, in intensive treatment schedules up to 4000 mg/qm, preferably up to up to 3000 mg/qm body surface area of cytarabine can be administered.

Dosage Forms and Formulation Aspects

Regarding any aspects of the invention for BI 6727 pharmaceutically acceptable salts or hydrates thereof may be used, preferably trihydrochloride salt forms and hydrates thereof as disclosed in WO 07/090,844. Dosages or amounts of the actives provided in the context of this invention refer in any case to the free base equivalent, that is BI 6727 in the free base form.

The term "therapeutically effective amount" shall mean that amount of a drug or pharmaceutical agent that will elicit the biological or medical response of a tissue system, animal or human that is being sought by a researcher or clinician, resulting in a beneficial effect for at least a statistically significant fraction of patients, such as a improvement of symptoms, a cure, a reduction in disease load, reduction in tumor mass or leukaemia cell numbers, extension of life, or improvement in quality of life.

Day 1 of a 4 week treatment cycle is defined as that day at which the first dose of BI 6727 or Cytarabine is administered.

The term "relapsed AML" is defined as reappearance of leukaemic blasts in the blood or >5% blasts in the bone marrow after CR (complete remission) not attributable to any other cause. For patients presenting with relapsed AML, >5% blasts on baseline bone marrow assessment is required.

The term "refractory AML" is defined as a failure to achieve a CR or CRi (complete remission with incomplete blood recovery) after previous therapy. Any number of prior anti-leukemia schedules is allowed.

The term "complete remission" is defined as morphologically leukaemia free state (i.e. bone marrow with <5% blasts by morphologic criteria and no Auer rods, no evidence of extramedullary leukaemia) and absolute neutrophil count ≥1,000/µL and platelets >100,000/µL.

The term "complete remission with incomplete blood recovery" is defined as morphologically leukaemia free state (i.e. bone marrow with <5% blasts by morphologic criteria and no Auer rods, no evidence of extramedullary leukaemia) and neutrophil count <1,000/μL or platelets <100,000 μL in the blood.

AML patients who are considered ineligible for intensive treatment constitute an accepted subgroup although no validated algorithm has been established to determine a patient's eligibility for intensive treatment. As reflected in current practice guidelines (NCCN Clinical practice Guidelines in Oncology™, Acute Myeloid Leukemia V.2.2021), the patient's age and duration of previous remission are important variables to assess a patient's eligibility for intensive treatment. However, many other factors will contribute to the medical assessment (e.g. AML cytogenetics, performance status, prior stem cell transplantation, concomitant diagnoses). Thus, an assessment of ineligibility for intensive treatment is required to ensure a defined and homogeneous patient population. This assessment will be performed for each patient and is based on a series of defined criteria identified through an extensive literature review of the prognostic factors predictive of an unfavourable outcome after treatment with intensive chemotherapy combination with different schedules of cytarabine and anthracycline Within the present invention the term "AML" is to be understood to encompass all forms of acute myeloid leukemia and related neoplasms according to the 2008 revision of the World Health Organization (WHO) classification of myeloid neoplasms and acute leukemia. Further all above mentioned subgroups in their relapsed or refractory state are encompassed. These are:

Acute myeloid leukemia with recurrent genetic abnormalities
   AML with t(8;21)(q22;q22); RUNX1-RUNX1T1
   AML with inv(16)(p13.1q22) or t(16;16)(p13.1;q22); CBFB-MYH11
   AML with t(9;11)(p22;q23); MLLT3-MLL
   AML with t(6;9)(p23;q34); DEK-NUP214
   AML with inv(3)(q21 q26.2) or t(3;3)(q21;q26.2); RPN1-EVI1
   AML (megakaryoblastic) with t(1;22)(p13;q13); RBM15-MKL1
   Provisional entity: AML with mutated NPM1
   Provisional entity: AML with mutated CEBPA
Acute myeloid leukemia with myelodysplasia-related changes
Therapy-related myeloid neoplasms
Acute myeloid leukemia, not otherwise specified
   AML with minimal differentiation
   AML without maturation
   AML with maturation
   Acute myelomonocytic leukemia
   Acute monoblastic/monocytic leukemia
   Acute erythroid leukemia
     Pure erythroid leukemia
     Erythroleukemia, erythroid/myeloid
   Acute megakaryoblastic leukemia
   Acute basophilic leukemia
   Acute panmyelosis with myelofibrosis
Myeloid sarcoma
Myeloid proliferations related to Down syndrome
   Transient abnormal myelopoiesis
   Myeloid leukemia associated with Down syndrome
Blastic plasmacytoid dendritic cell neoplasm In accordance with the present invention BI 6727 may be administered by parenteral (e.g. intramuscular, intraperitoneal, intravenous, transdermal or subcutaneous injection), and may be formulated, alone or together, in suitable dosage unit formulations containing conventional non-toxic pharmaceutically acceptable carriers, adjuvants and vehicles appropriate for each route of administration. Dosage forms and formulations of both actives suitable within the present invention are known in the art. For instance, such dosage forms and formulations include those disclosed for BI 6727 in WO 2006/018221.

In accordance with the present invention Cytarabine may be administered by parenteral (e.g. intramuscular, intraperitoneal, intravenous, transdermal or subcutaneous injection, or implant), routes of administration and may be formulated, alone or together, in suitable dosage unit formulations containing conventional non-toxic pharmaceutically acceptable carriers, adjuvants and vehicles appropriate for each route of administration.

The following Examples serve to illustrate the invention without restricting it:

Example: Clinical Trial

Methods:

BI 6727 (350 mg) was administered as a one-hour intravenous infusion on Days 1+15 every 28 days in combination with fixed dose LD-Ara-C (low-dose cytarabine) (20 mg twice daily s.c. [subcutaneous]). The starting dose of BI 6727 was based on the MTD previously determined in solid tumor patients. Patients with no progression after the first cycle were allowed to continue treatment.

Results:

Increasing BI 6727 doses in combination with LD-Ara-C were evaluated in 32 patients (21 males, 11 females). Patient characteristics were as follows: median age 71 years (range 40-81); Eastern Cooperative Oncology Group performance score: 0: nine patients; 1: 18 patients; 2: five patients. Safety: Drug-related adverse events (AEs) were reported in 18 of the 32 patients (56.3%). The most frequent drug-related AEs reported (>5%) were: anemia, diarrhea, febrile neutropenia and nausea which were 9.7% each), and decreased appetite, headache, mucositis and pain in extremity (each 6.5%). Dose-limiting toxicities (DLTs) were reported in four patients treated with BI 6727+LD-Ara-C. DLTs as rated per protocol were: pneumonia, mucositis, hypersensitivity/allergic reaction and myocardial infarction. Based on the DLTs the MTD for BI 6727 (d1+15q28d) in combination with LD-Ara-C was determined to be 350 mg.

Efficacy:

Preliminary best response data of 32 patients with relapsed/refractory AML treated at different BI 6727 doses in combination with LD-Ara-C are available: seven patients achieved a incomplete blood count recovery (CRi) or complete remission (CR), 1 patients achieved a partial remission. Six patients had temporarily stable blood values ("no change" as best response). Eleven patients suffered from progression during or at the end of the first-treatment cycle, and seven patients had no response assessment (inedetermined).

CONCLUSIONS

Results indicate that BI 6727 in combination with LD-Ara-C is well tolerated in patients with relapsed/refractory AML ineligible for intensive treatment. The MTD of BI 6727 in combination with LD-Ara-C was determined at 350 mg. BI 6727 in combination with LD-Ara-C showed first signs of clinical activity in AML patients.

The invention claimed is:
1. A method of treating acute myeloid leukemia (AML) comprising a) administering an effective amount of BI 6727 or a pharmaceutically acceptable salt thereof or a hydrate thereof at least two days during a 4 week treatment cycle and
b) administering an effective amount of Cytarabine for 10 days of the said 4 week treatment cycle to a patient suffering from AML.

2. The method according to claim 1, wherein BI 6727 or a pharmaceutically acceptable salt thereof or a hydrate thereof is administered at day 1 and at one of the days 7, 8, 9, 10, 11, 12, 13, 14, 15, 16, 17, 18, 19, 20 or 21 during a 4 week treatment cycle.

3. The method according to claim 1, wherein 350 to 500 mg of BI 6727 or a pharmaceutically acceptable salt thereof or a hydrate thereof are administered per day of administration.

4. The method according to claim 1, wherein Cytarabine is administered from day 1 to 10 of the said 4 week treatment cycle.

5. The method according to claim 1, wherein 40 mg Cytarabine are administered per day of administration.

6. The method according to claim 1, wherein the AML is relapsed AML.

7. The method according to claim 1 wherein the AML is refractory AML.

8. The method according to claim 1 wherein the patient suffering from AML is ineligible for intensive treatment.

9. The method according to claim 1, wherein BI 6727 or a pharmaceutically acceptable salt thereof or a hydrate thereof is administered at 350 mg/application.

\* \* \* \* \*